Nov. 17, 1936. P. SCHMIDT Plant Pat. 206
BUDDLEIA
Filed Nov. 15, 1935
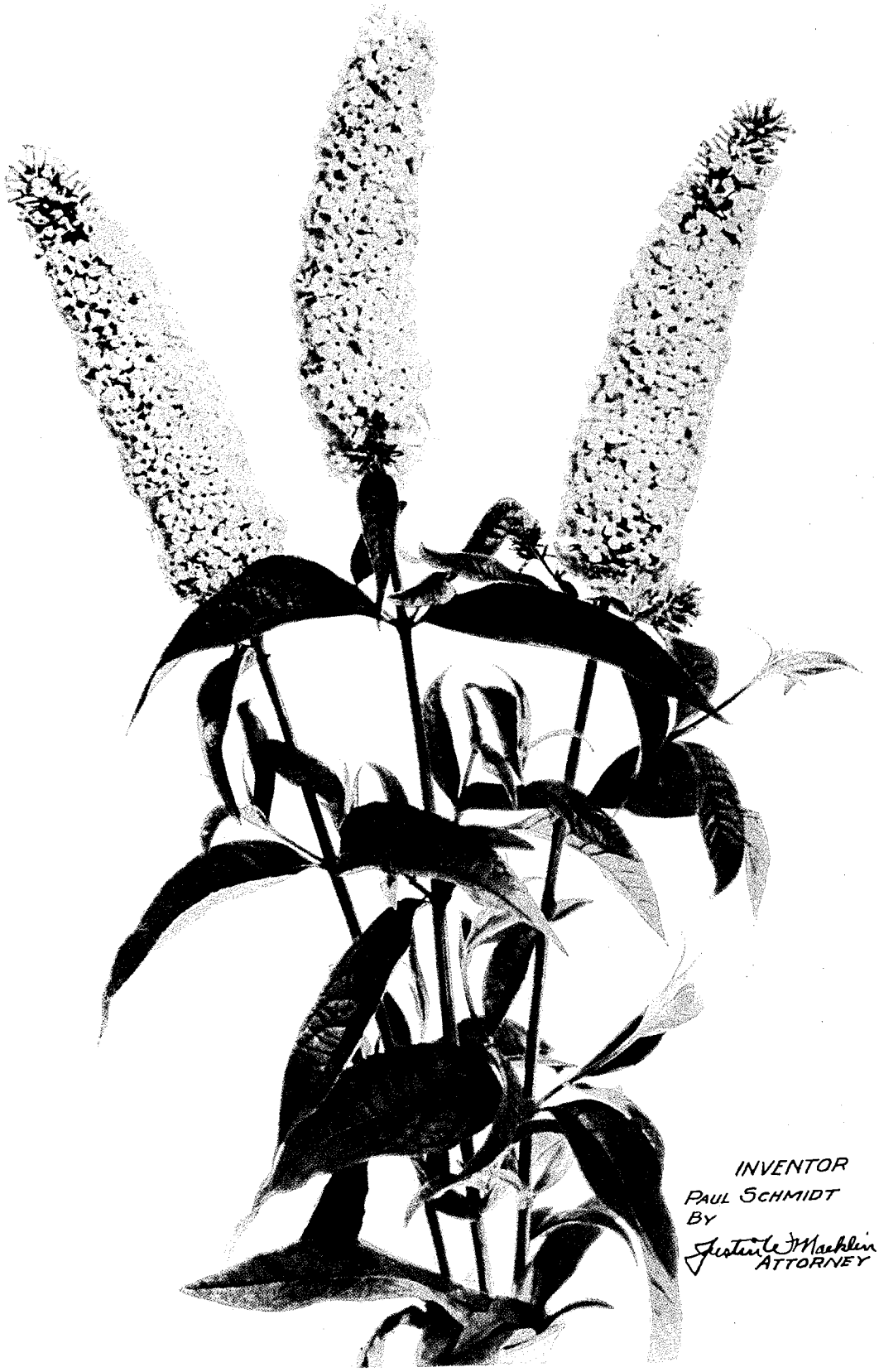
INVENTOR
PAUL SCHMIDT
BY
Justus E. Maehlen
ATTORNEY Patented Nov. 17, 1936

Plant Pat. 206

UNITED STATES PATENT OFFICE

206

BUDDLEIA

Paul Schmidt, Youngstown, Ohio

Application November 15, 1935, Serial No. 49,982

1 Claim. (Cl. 47—60)

This invention relates to a new type of Buddleia flower and a method of reproducing this flower.

The object of my invention is to produce a type of Buddleia having a rich, heavy, dark green foliage with an abundance of flower clusters or panicles.

A further object of this invention is to produce a type of Buddleia which will have the flower portion in full bloom the length of the panicle all at one time.

Another object is to produce a panicle which is completely or almost round in the same manner as a cluster of blooms of the lilac, and not a flat or one-sided panicle as usually grows on a Buddleia.

Another object of this invention is to produce a type of Buddleia which is unique in character, attractive in form and color, of pleasant fragrance, and which can be asexually reproduced.

Another object is to produce a Buddleia, the flowers of which last a long time in water when cut, and which does not wilt at the tips of the panicles.

My invention consists in the production of a new variety of Buddleia which was accomplished by a cross between the varieties Magnifica and Farquarii, the former being the male parent and the latter the female parent. This variety of Buddleia has flower panicles on the main or terminal stock of an increased length over that of both parents, and has lateral flower panicles which are noticeably longer and of the same characteristics as the terminal flower panicles.

This new Buddleia is distinguishable in its color in that the panicles are of a violet-lilac color corresponding to Plate No. 41E5 of Maerz and Paul, often having a cast or hue of a rosy-lilac, Plate No. 3G7, which is aided by the brilliant orange-peel centers, Plate No. 10L10, of the small flowers, hundreds of which form the flower panicle.

The long panicles are distinguished from the common Buddleia in that the panicle is in full bloom throughout its entire length at one time in contrast with its parent Buddleia, which has a wilted lower portion of the panicle when the tip of the same panicle is in full bloom. The panicle of this new type of Buddleia is further distinguished over others in that it comprises a denser group of blossoms throughout the length of the panicle or spray. These blossoms are set more closely together and are grouped around the flower stem, producing a comparatively circular flower spray of great length.

The stems supporting the panicles of this flower are very sturdy and have an apparently smooth outer surface of a dark green color. The foliage supported by the stems approaches that of a velvety texture because of its dark green upper surface and its silver green under surface. The foliage is abundant and characteristically clean in appearance.

Further propagation of this plant is accomplished by making cuttings from the many side shoots on the stem below the bloom.

In the accompanying drawing is illustrated a group of three of this newly developed type of Buddleia illustrating the process of the blooming of the panicle from the bottom or lower portion of the bloom head to the upper. The center panicle illustrates the Buddleia in full bloom with no wilted portion throughout its entire length. The remaining panicles illustrate the flower before full bloom. However, it should be understood that upon severance of the panicle from the plant before a condition of full bloom, the panicle will continue blooming until such full bloom condition is reached.

The drawing further illustrates many of the characteristics which are not to be found in the parent Buddleia and which make the flower of more value as a plant and enhance its aesthetic value.

Having now fully shown and described my new type of Buddleia and the mode of its production, what I claim and desire to secure by Letters Patent of the United States is:

A Buddleia as herein shown and described and distinguished by rich heavy dark green foliage, great abundance of flower panicles or bloom heads normally larger and having more circularity than the bloom heads of either of the parent Buddleia and the panicles being of a lilac color, and having characteristics making it more suitable for use as a cut flower.

PAUL SCHMIDT.